(12) United States Patent
Guerra

(10) Patent No.: US 7,922,953 B2
(45) Date of Patent: Apr. 12, 2011

(54) METHOD FOR MANUFACTURING AN END EFFECTOR ASSEMBLY

(75) Inventor: Paul Guerra, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 750 days.

(21) Appl. No.: 11/529,414

(22) Filed: Sep. 28, 2006

(65) Prior Publication Data

US 2007/0074807 A1 Apr. 5, 2007

Related U.S. Application Data

(60) Provisional application No. 60/722,186, filed on Sep. 30, 2005.

(51) Int. Cl.
B29C 45/14 (2006.01)
B29B 13/00 (2006.01)
A61B 18/18 (2006.01)

(52) U.S. Cl. .................... 264/272.11; 264/259; 264/263; 264/265; 264/271.1; 606/45; 606/48; 606/49

(58) Field of Classification Search .................. 264/259, 264/264, 271.1, 249, 275, 279.1
See application file for complete search history.

(56) References Cited

U.S. PATENT DOCUMENTS

| | | | |
|---|---|---|---|
| 371,664 | A | 10/1887 | Brannan et al. |
| 702,472 | A | 6/1902 | Pignolet |
| 728,883 | A | 5/1903 | Downes |
| 1,586,645 | A | 6/1926 | Bierman |
| 1,813,902 | A | 7/1931 | Bovie |
| 1,822,330 | A | 9/1931 | Ainslie |
| 1,852,542 | A | 4/1932 | Sovatkin |
| 2,002,594 | A | 5/1935 | Wappler et al. |
| 2,011,169 | A | 8/1935 | Wappler |
| 2,031,682 | A | 2/1936 | Wappler et al. |
| 2,054,149 | A | 9/1936 | Wappler |
| 2,176,479 | A | 10/1939 | Willis |
| 2,305,156 | A | 4/1941 | Grubel |
| 2,279,753 | A | 4/1942 | Knopp |

(Continued)

FOREIGN PATENT DOCUMENTS

CA 2104423 2/1994

(Continued)

OTHER PUBLICATIONS

Int'l Search Report EP 04 752343.6 dated Jul. 20, 2007.

(Continued)

*Primary Examiner* — Christina Johnson
*Assistant Examiner* — Benjamin Schiffman

(57) ABSTRACT

A method of manufacturing a jaw member of an end effector assembly for use with an electrosurgical instrument is disclosed that includes the steps of providing an electrically conductive tissue engaging plate and a jaw support; covering one side of the electrically conductive tissue engaging plate with an electrically insulative, thermally non-degrading coating; placing and securing the electrically conductive tissue engaging plate and the jaw support into a jaw mold; and introducing a liquid substance into the jaw mold and allowing the liquid substance to cure around the electrically conductive tissue engaging plate and the jaw support. Alternatively, the method includes the steps of: providing an electrically conductive tissue engaging plate and a jaw support; covering one side of the electrically conductive tissue engaging plate with an electrically insulative, thermally non-degrading coating; and securing the side of the electrically conductive tissue engaging plate onto the jaw support with an adhesive.

4 Claims, 8 Drawing Sheets

U.S. PATENT DOCUMENTS

| | | |
|---|---|---|
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Xamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |

| | | | | | |
|---|---|---|---|---|---|
| 5,405,344 A | 4/1995 | Williamson et al. | 5,603,711 A | 2/1997 | Parins et al. |
| 5,409,763 A | 4/1995 | Serizawa et al. | 5,603,723 A | 2/1997 | Aranyi et al. |
| 5,411,519 A | 5/1995 | Tovey et al. | 5,611,798 A | 3/1997 | Eggers |
| 5,411,520 A | 5/1995 | Nash et al. | 5,611,808 A | 3/1997 | Hossain et al. |
| 5,413,571 A | 5/1995 | Katsaros et al. | 5,611,813 A | 3/1997 | Lichtman |
| 5,415,656 A | 5/1995 | Tihon et al. | 5,620,415 A | 4/1997 | Lucey et al. |
| 5,415,657 A | 5/1995 | Taymor-Luria | 5,620,453 A | 4/1997 | Nallakrishnan |
| 5,422,567 A | 6/1995 | Matsunaga | 5,620,459 A | 4/1997 | Lichtman |
| 5,423,810 A | 6/1995 | Goble et al. | 5,624,452 A | 4/1997 | Yates |
| 5,425,690 A | 6/1995 | Chang | 5,626,578 A | 5/1997 | Tihon |
| 5,425,739 A | 6/1995 | Jessen | 5,626,609 A | 5/1997 | Zvenyatsky et al. |
| 5,429,616 A | 7/1995 | Schaffer | 5,630,833 A | 5/1997 | Katsaros et al. |
| 5,431,672 A | 7/1995 | Cote et al. | 5,637,110 A | 6/1997 | Pennybacker et al. |
| 5,431,674 A | 7/1995 | Basile et al. | 5,638,003 A | 6/1997 | Hall |
| 5,437,292 A | 8/1995 | Kipshidze et al. | 5,643,294 A | 7/1997 | Tovey et al. |
| 5,438,302 A | 8/1995 | Goble | 5,647,869 A | 7/1997 | Goble et al. |
| 5,439,478 A | 8/1995 | Palmer | 5,647,871 A | 7/1997 | Levine et al. |
| 5,441,517 A | 8/1995 | Kensey et al. | 5,649,959 A | 7/1997 | Hannam et al. |
| 5,443,463 A | 8/1995 | Stern et al. | 5,655,650 A | 8/1997 | Naitou |
| 5,443,464 A | 8/1995 | Russell et al. | 5,658,281 A | 8/1997 | Heard |
| 5,443,480 A | 8/1995 | Jacobs et al. | D384,413 S | 9/1997 | Zlock et al. |
| 5,445,638 A | 8/1995 | Rydell et al. | 5,662,667 A | 9/1997 | Knodel |
| 5,445,658 A | 8/1995 | Durrfeld et al. | 5,665,100 A | 9/1997 | Yoon |
| 5,449,480 A * | 9/1995 | Kuriya et al. ................ 264/112 | 5,667,526 A | 9/1997 | Levin |
| 5,451,224 A | 9/1995 | Goble et al. | 5,674,220 A | 10/1997 | Fox et al. |
| 5,454,823 A | 10/1995 | Richardson et al. | 5,674,229 A | 10/1997 | Tovey et al. |
| 5,454,827 A | 10/1995 | Aust et al. | 5,681,282 A | 10/1997 | Eggers et al. |
| 5,456,684 A | 10/1995 | Schmidt et al. | 5,688,270 A | 11/1997 | Yates et al. |
| 5,458,598 A | 10/1995 | Feinberg et al. | 5,690,652 A | 11/1997 | Wurster et al. |
| 5,460,629 A | 10/1995 | Shlain et al. | 5,690,653 A | 11/1997 | Richardson et al. |
| 5,461,765 A | 10/1995 | Linden et al. | 5,693,051 A | 12/1997 | Schulze et al. |
| 5,462,546 A | 10/1995 | Rydell | 5,693,920 A | 12/1997 | Maeda |
| 5,472,442 A | 12/1995 | Klicek | 5,695,522 A | 12/1997 | LeMaire, III et al. |
| 5,472,443 A | 12/1995 | Cordis et al. | 5,700,261 A | 12/1997 | Brinkerhoff |
| 5,478,351 A | 12/1995 | Meade et al. | 5,700,270 A | 12/1997 | Peyser et al. |
| 5,480,406 A | 1/1996 | Nolan et al. | 5,702,390 A | 12/1997 | Austin et al. |
| 5,480,409 A | 1/1996 | Riza | 5,707,369 A | 1/1998 | Vaitekunas et al. |
| 5,484,436 A | 1/1996 | Eggers et al. | 5,709,680 A | 1/1998 | Yates et al. |
| 5,496,312 A | 3/1996 | Klicek | 5,716,366 A | 2/1998 | Yates |
| 5,496,317 A | 3/1996 | Goble et al. | 5,720,744 A | 2/1998 | Eggleston et al. |
| 5,496,347 A | 3/1996 | Hashiguchi et al. | 5,722,421 A | 3/1998 | Francese et al. |
| 5,499,997 A | 3/1996 | Sharpe et al. | 5,725,536 A | 3/1998 | Oberlin et al. |
| 5,509,922 A | 4/1996 | Aranyi et al. | 5,727,428 A | 3/1998 | LeMaire, III et al. |
| 5,514,134 A | 5/1996 | Rydell et al. | 5,735,848 A | 4/1998 | Yates et al. |
| 5,527,313 A | 6/1996 | Scott et al. | 5,743,906 A | 4/1998 | Parins et al. |
| 5,528,833 A * | 6/1996 | Sakuma ................ 30/260 | 5,752,973 A | 5/1998 | Kieturakis |
| 5,529,067 A | 6/1996 | Larsen et al. | 5,755,717 A | 5/1998 | Yates et al. |
| 5,531,744 A | 7/1996 | Nardella et al. | 5,759,188 A | 6/1998 | Yoon |
| 5,536,251 A | 7/1996 | Evard et al. | 5,766,130 A | 6/1998 | Selmonosky |
| 5,540,684 A | 7/1996 | Hassler, Jr. | 5,766,166 A | 6/1998 | Hooven |
| 5,540,685 A | 7/1996 | Parins et al. | 5,766,170 A | 6/1998 | Eggers |
| 5,540,706 A | 7/1996 | Aust et al. | 5,766,196 A | 6/1998 | Griffiths |
| 5,540,715 A | 7/1996 | Katsaros et al. | 5,769,849 A | 6/1998 | Eggers |
| 5,542,945 A | 8/1996 | Fritzsch | 5,772,655 A | 6/1998 | Bauer et al. |
| 5,558,671 A | 9/1996 | Yates | 5,772,670 A | 6/1998 | Brosa |
| 5,558,672 A | 9/1996 | Edwards et al. | 5,776,128 A | 7/1998 | Eggers |
| 5,562,619 A | 10/1996 | Mirarchi et al. | 5,776,130 A | 7/1998 | Buysse et al. |
| 5,562,699 A | 10/1996 | Heimberger et al. | 5,779,646 A | 7/1998 | Koblish et al. |
| 5,562,720 A | 10/1996 | Stern et al. | 5,779,701 A | 7/1998 | McBrayer et al. |
| 5,564,615 A | 10/1996 | Bishop et al. | H1745 H | 8/1998 | Paraschac |
| 5,569,241 A | 10/1996 | Edwardds | 5,792,137 A | 8/1998 | Carr et al. |
| 5,569,243 A | 10/1996 | Kortenbach et al. | 5,792,165 A | 8/1998 | Klieman et al. |
| 5,571,100 A | 11/1996 | Goble et al. | 5,792,177 A | 8/1998 | Kaseda |
| 5,573,424 A | 11/1996 | Poppe | 5,797,537 A | 8/1998 | Oberlin et al. |
| 5,573,534 A | 11/1996 | Stone | 5,797,927 A | 8/1998 | Yoon |
| 5,573,535 A | 11/1996 | Viklund | 5,797,938 A | 8/1998 | Paraschac et al. |
| 5,575,799 A | 11/1996 | Bolanos et al. | 5,797,941 A | 8/1998 | Schulze et al. |
| 5,575,805 A | 11/1996 | Li | 5,797,958 A | 8/1998 | Yoon |
| 5,578,052 A | 11/1996 | Koros et al. | 5,800,449 A | 9/1998 | Wales |
| 5,579,781 A | 12/1996 | Cooke | 5,807,393 A | 9/1998 | Williamson, IV et al. |
| 5,582,611 A | 12/1996 | Tsukagoshi et al. | 5,810,764 A | 9/1998 | Eggers et al. |
| 5,582,617 A | 12/1996 | Klieman et al. | 5,810,805 A | 9/1998 | Sutcu et al. |
| 5,585,896 A | 12/1996 | Yamazaki et al. | 5,810,808 A | 9/1998 | Eggers |
| 5,590,570 A | 1/1997 | LeMaire, III et al. | 5,810,811 A | 9/1998 | Yates et al. |
| 5,591,181 A | 1/1997 | Stone et al. | 5,810,877 A | 9/1998 | Roth et al. |
| 5,597,107 A | 1/1997 | Knodel et al. | 5,814,043 A | 9/1998 | Shapeton |
| 5,601,224 A | 2/1997 | Bishop et al. | 5,814,054 A | 9/1998 | Kortenbach et al. |
| 5,601,601 A | 2/1997 | Tal et al. | 5,817,093 A | 10/1998 | Williamson, IV et al. |
| 5,601,641 A | 2/1997 | Stephens | 5,817,119 A | 10/1998 | Klieman et al. |

| | | | | | | |
|---|---|---|---|---|---|---|
| 5,820,630 A | 10/1998 | Lind | | 6,086,586 A | 7/2000 | Hooven |
| 5,824,978 A | 10/1998 | Karasik et al. | | 6,086,601 A | 7/2000 | Yoon |
| 5,827,271 A | 10/1998 | Buysse et al. | | 6,090,107 A | 7/2000 | Borgmeier et al. |
| 5,827,279 A | 10/1998 | Hughett et al. | | 6,096,037 A | 8/2000 | Mulier et al. |
| 5,827,281 A | 10/1998 | Levin | | 6,099,550 A | 8/2000 | Yoon |
| 5,827,323 A | 10/1998 | Klieman et al. | | 6,102,909 A | 8/2000 | Chen et al. |
| 5,827,548 A | 10/1998 | Lavallee et al. | | 6,106,542 A | 8/2000 | Toybin et al. |
| 5,833,690 A | 11/1998 | Yates et al. | | 6,110,171 A | 8/2000 | Rydell |
| 5,843,080 A | 12/1998 | Fleenor et al. | | 6,113,596 A | 9/2000 | Hooven et al. |
| 5,849,022 A | 12/1998 | Sakashita et al. | | 6,113,598 A | 9/2000 | Baker |
| 5,853,412 A | 12/1998 | Mayenberger | | 6,117,158 A | 9/2000 | Measamer et al. |
| 5,859,527 A | 1/1999 | Cook | | 6,122,549 A | 9/2000 | Sharkey et al. |
| 5,860,976 A | 1/1999 | Billings et al. | | 6,123,701 A | 9/2000 | Nezhat |
| 5,876,401 A | 3/1999 | Schulze et al. | | H1904 H | 10/2000 | Yates et al. |
| 5,876,412 A | 3/1999 | Piraka | | 6,126,658 A | 10/2000 | Baker |
| 5,882,567 A | 3/1999 | Cavallaro et al. | | 6,126,665 A | 10/2000 | Yoon |
| 5,891,141 A | 4/1999 | Rydell | | 6,139,563 A | 10/2000 | Cosgrove, III et al. |
| 5,891,142 A | 4/1999 | Eggers et al. | | 6,143,005 A | 11/2000 | Yoon et al. |
| 5,893,863 A | 4/1999 | Yoon | | 6,152,923 A | 11/2000 | Ryan |
| 5,893,875 A | 4/1999 | O'Connor et al. | | 6,162,220 A | 12/2000 | Nezhat |
| 5,893,877 A | 4/1999 | Gampp, Jr. et al. | | 6,171,316 B1 | 1/2001 | Kovac et al. |
| 5,897,563 A | 4/1999 | Yoon et al. | | 6,174,309 B1 | 1/2001 | Wrublewski et al. |
| 5,902,301 A | 5/1999 | Olig | | 6,178,628 B1 | 1/2001 | Clemens et al. |
| 5,906,630 A | 5/1999 | Anderhub et al. | | 6,179,834 B1 | 1/2001 | Buysse et al. |
| 5,908,420 A | 6/1999 | Parins et al. | | 6,179,837 B1 | 1/2001 | Hooven |
| 5,908,432 A | 6/1999 | Pan | | 6,183,467 B1 | 2/2001 | Shapeton et al. |
| 5,911,719 A | 6/1999 | Eggers | | 6,187,003 B1 | 2/2001 | Buysse et al. |
| 5,913,874 A | 6/1999 | Berns et al. | | 6,190,386 B1 | 2/2001 | Rydell |
| 5,921,916 A | 7/1999 | Aeikens et al. | | 6,190,400 B1 | 2/2001 | Vandemoer et al. |
| 5,921,984 A | 7/1999 | Sutcu et al. | | 6,193,718 B1 | 2/2001 | Kortenbach et al. |
| 5,925,043 A | 7/1999 | Kumar et al. | | 6,206,876 B1 | 3/2001 | Levine et al. |
| 5,928,136 A | 7/1999 | Barry | | 6,206,877 B1 | 3/2001 | Kese et al. |
| 5,935,126 A | 8/1999 | Riza | | 6,206,893 B1 | 3/2001 | Klein et al. |
| 5,941,869 A | 8/1999 | Patterson et al. | | 6,214,028 B1 | 4/2001 | Yoon et al. |
| 5,944,718 A | 8/1999 | Dafforn et al. | | 6,217,602 B1 | 4/2001 | Redmon |
| 5,951,546 A | 9/1999 | Lorentzen | | 6,217,615 B1 | 4/2001 | Sioshansi et al. |
| 5,951,549 A | 9/1999 | Richardson et al. | | 6,221,039 B1 | 4/2001 | Durgin et al. |
| 5,954,720 A | 9/1999 | Wilson et al. | | 6,223,100 B1 | 4/2001 | Green |
| 5,954,731 A | 9/1999 | Yoon | | 6,224,593 B1 | 5/2001 | Ryan et al. |
| 5,954,733 A | 9/1999 | Yoon | | 6,224,614 B1 | 5/2001 | Yoon |
| 5,957,923 A | 9/1999 | Hahnen et al. | | 6,228,080 B1 | 5/2001 | Gines |
| 5,957,937 A | 9/1999 | Yoon | | 6,228,083 B1 | 5/2001 | Lands et al. |
| 5,960,544 A | 10/1999 | Beyers | | 6,248,124 B1 | 6/2001 | Pedros et al. |
| 5,961,514 A | 10/1999 | Long et al. | | 6,248,944 B1 | 6/2001 | Ito |
| 5,964,758 A | 10/1999 | Dresden | | 6,261,307 B1 | 7/2001 | Yoon et al. |
| 5,976,132 A | 11/1999 | Morris | | 6,267,761 B1 | 7/2001 | Ryan |
| 5,984,932 A | 11/1999 | Yoon | | 6,270,497 B1 | 8/2001 | Sekino et al. |
| 5,984,938 A | 11/1999 | Yoon | | 6,270,508 B1 | 8/2001 | Klieman et al. |
| 5,984,939 A | 11/1999 | Yoon | | 6,273,887 B1 | 8/2001 | Yamauchi et al. |
| 5,989,277 A | 11/1999 | LeMaire, III et al. | | 6,277,117 B1 | 8/2001 | Tetzlaff et al. |
| 5,993,466 A | 11/1999 | Yoon | | 6,280,458 B1 | 8/2001 | Boche et al. |
| 5,993,467 A | 11/1999 | Yoon | | 6,283,961 B1 | 9/2001 | Underwood et al. |
| 5,997,565 A | 12/1999 | Inoue | | D449,886 S | 10/2001 | Tetzlaff et al. |
| 6,004,332 A | 12/1999 | Yoon et al. | | 6,298,550 B1 | 10/2001 | Kirwan |
| 6,004,335 A | 12/1999 | Vaitekunas et al. | | 6,302,424 B1 | 10/2001 | Gisinger et al. |
| 6,010,516 A | 1/2000 | Hulka et al. | | 6,319,262 B1 | 11/2001 | Bates et al. |
| 6,017,358 A | 1/2000 | Yoon et al. | | 6,319,451 B1 | 11/2001 | Brune |
| 6,021,693 A * | 2/2000 | Feng-Sing ............... 76/106.5 | | 6,322,561 B1 | 11/2001 | Eggers et al. |
| 6,024,741 A | 2/2000 | Williamson et al. | | 6,322,580 B1 | 11/2001 | Kanner |
| 6,024,743 A | 2/2000 | Edwards | | 6,325,795 B1 | 12/2001 | Lindemann et al. |
| 6,024,744 A | 2/2000 | Kese et al. | | 6,334,860 B1 | 1/2002 | Dorn |
| 6,027,522 A | 2/2000 | Palmer | | 6,334,861 B1 | 1/2002 | Chandler et al. |
| 6,030,384 A | 2/2000 | Nezhat | | 6,345,532 B1 | 2/2002 | Coudray et al. |
| 6,033,399 A | 3/2000 | Gines | | 6,350,264 B1 | 2/2002 | Hooven |
| 6,039,733 A | 3/2000 | Buysse et al. | | 6,352,536 B1 | 3/2002 | Buysse et al. |
| 6,041,679 A | 3/2000 | Slater et al. | | 6,358,249 B1 | 3/2002 | Chen et al. |
| 6,050,996 A | 4/2000 | Schmaltz et al. | | 6,358,259 B1 | 3/2002 | Swain et al. |
| 6,053,914 A | 4/2000 | Eggers et al. | | 6,358,268 B1 | 3/2002 | Hunt et al. |
| 6,053,933 A | 4/2000 | Balazs et al. | | 6,364,879 B1 | 4/2002 | Chen et al. |
| D424,694 S | 5/2000 | Tetzlaff et al. | | D457,958 S | 5/2002 | Dycus et al. |
| D425,201 S | 5/2000 | Tetzlaff et al. | | D457,959 S | 5/2002 | Tetzlaff et al. |
| 6,059,782 A | 5/2000 | Novak et al. | | 6,387,094 B1 | 5/2002 | Eitenmuller |
| 6,066,139 A | 5/2000 | Ryan et al. | | 6,391,035 B1 | 5/2002 | Appleby et al. |
| 6,071,283 A * | 6/2000 | Nardella et al. ............. 606/46 | | 6,398,779 B1 | 6/2002 | Buysse et al. |
| 6,074,386 A | 6/2000 | Goble et al. | | 6,402,747 B1 | 6/2002 | Lindemann et al. |
| 6,077,287 A | 6/2000 | Taylor et al. | | 6,409,728 B1 | 6/2002 | Ehr et al. |
| 6,080,180 A | 6/2000 | Yoon et al. | | H2037 H | 7/2002 | Yates et al. |
| RE36,795 E | 7/2000 | Rydell | | 6,419,675 B1 | 7/2002 | Gallo, Sr. |
| 6,083,223 A | 7/2000 | Baker | | 6,425,896 B1 | 7/2002 | Baltschun et al. |

| | | | |
|---|---|---|---|
| 6,432,112 B2 | 8/2002 | Brock et al. | |
| 6,440,144 B1 | 8/2002 | Bacher | |
| 6,443,952 B1 | 9/2002 | Mulier et al. | |
| 6,443,970 B1 | 9/2002 | Schulze et al. | |
| 6,451,018 B1 | 9/2002 | Lands et al. | |
| 6,458,125 B1 | 10/2002 | Cosmescu | |
| 6,458,128 B1 | 10/2002 | Schulze | |
| 6,458,130 B1 | 10/2002 | Frazier et al. | |
| 6,461,352 B2 | 10/2002 | Morgan et al. | |
| 6,461,368 B2 | 10/2002 | Fogarty et al. | |
| 6,464,701 B1 | 10/2002 | Hooven et al. | |
| 6,464,702 B2 | 10/2002 | Schulze et al. | |
| 6,464,704 B2 | 10/2002 | Schmaltz et al. | |
| 6,485,489 B2 | 11/2002 | Teirstein et al. | |
| 6,494,888 B1 | 12/2002 | Laufer et al. | |
| 6,500,176 B1 | 12/2002 | Truckai et al. | |
| 6,506,196 B1 | 1/2003 | Laufer | |
| 6,508,815 B1 | 1/2003 | Strul et al. | |
| 6,511,480 B1 | 1/2003 | Tetzlaff et al. | |
| 6,514,215 B1 | 2/2003 | Ouchi | |
| 6,514,252 B2 | 2/2003 | Nezhat et al. | |
| 6,517,539 B1 | 2/2003 | Smith et al. | |
| 6,527,771 B1 | 3/2003 | Weadock et al. | |
| 6,533,784 B2 | 3/2003 | Truckai et al. | |
| 6,545,239 B2 | 4/2003 | Spedale et al. | |
| 6,558,385 B1 | 5/2003 | McClurken et al. | |
| 6,562,037 B2 | 5/2003 | Paton et al. | |
| 6,569,105 B1 | 5/2003 | Kortenbach et al. | |
| 6,582,450 B2 | 6/2003 | Ouchi | |
| 6,585,735 B1 | 7/2003 | Frazier et al. | |
| 6,602,252 B2 | 8/2003 | Mollenauer | |
| 6,605,790 B2 | 8/2003 | Yoshida | |
| 6,616,658 B2 | 9/2003 | Ineson | |
| 6,616,661 B2 | 9/2003 | Wellman et al. | |
| 6,620,161 B2 | 9/2003 | Schulze et al. | |
| 6,620,184 B2 | 9/2003 | De Laforcade et al. | |
| 6,626,901 B1 | 9/2003 | Treat et al. | |
| 6,638,287 B2 | 10/2003 | Danitz et al. | |
| 6,641,595 B1 | 11/2003 | Moran et al. | |
| 6,652,514 B2 | 11/2003 | Ellman et al. | |
| 6,652,521 B2 | 11/2003 | Schulze | |
| 6,656,175 B2 | 12/2003 | Francischelli et al. | |
| 6,656,177 B2 | 12/2003 | Truckai et al. | |
| 6,660,072 B2 | 12/2003 | Chatterjee | |
| 6,663,639 B1 | 12/2003 | Laufer et al. | |
| 6,663,641 B1 | 12/2003 | Kovac et al. | |
| 6,666,854 B1 | 12/2003 | Lange | |
| 6,669,696 B2 | 12/2003 | Bacher et al. | |
| 6,673,092 B1 | 1/2004 | Bacher | |
| 6,676,660 B2 | 1/2004 | Wampler et al. | |
| 6,676,676 B2 | 1/2004 | Danitz et al. | |
| 6,679,882 B1 | 1/2004 | Kornerup | |
| 6,682,527 B2 | 1/2004 | Strul | |
| 6,682,528 B2 | 1/2004 | Frazier et al. | |
| 6,685,724 B1 | 2/2004 | Haluck | |
| 6,689,131 B2 | 2/2004 | McClurken | |
| 6,692,445 B2 | 2/2004 | Roberts et al. | |
| 6,693,246 B1 | 2/2004 | Rudolph et al. | |
| 6,695,840 B2 | 2/2004 | Schulze | |
| 6,702,810 B2 | 3/2004 | McClurken et al. | |
| 6,723,092 B2 | 4/2004 | Brown et al. | |
| 6,726,068 B2 | 4/2004 | Miller | |
| 6,726,686 B2 | 4/2004 | Buysse et al. | |
| 6,726,694 B2 | 4/2004 | Blatter et al. | |
| 6,733,498 B2 | 5/2004 | Paton et al. | |
| 6,736,813 B2 | 5/2004 | Yamauchi et al. | |
| 6,743,229 B2 | 6/2004 | Buysse et al. | |
| 6,743,230 B2 | 6/2004 | Lutze et al. | |
| 6,743,239 B1 | 6/2004 | Kuehn et al. | |
| 6,743,240 B2 | 6/2004 | Smith et al. | |
| 6,755,843 B2 | 6/2004 | Chung et al. | |
| 6,756,553 B1 | 6/2004 | Yamaguchi et al. | |
| 6,757,977 B2 | 7/2004 | Dambal et al. | |
| D493,888 S | 8/2004 | Reschke | |
| 6,770,072 B1 | 8/2004 | Truckai et al. | |
| 6,773,409 B2 | 8/2004 | Truckai et al. | |
| 6,773,432 B1 | 8/2004 | Clayman et al. | |
| 6,773,434 B2 | 8/2004 | Ciarrocca | |
| 6,773,441 B1 | 8/2004 | Laufer et al. | |
| 6,775,575 B2 | 8/2004 | Bommannan et al. | |
| 6,776,780 B2 | 8/2004 | Mulier et al. | |
| 6,786,905 B2 | 9/2004 | Swanson et al. | |
| 6,790,217 B2 | 9/2004 | Schulze et al. | |
| 6,796,981 B2 | 9/2004 | Wham et al. | |
| D496,997 S | 10/2004 | Dycus et al. | |
| 6,800,825 B1 | 10/2004 | Sasaki et al. | |
| 6,802,843 B2 | 10/2004 | Truckai et al. | |
| 6,808,525 B2 | 10/2004 | Latterell et al. | |
| D499,181 S | 11/2004 | Dycus et al. | |
| 6,818,000 B2 | 11/2004 | Muller et al. | |
| 6,821,285 B2 | 11/2004 | Laufer et al. | |
| 6,835,200 B2 | 12/2004 | Laufer et al. | |
| 6,857,357 B2 | 2/2005 | Fujii | |
| 6,860,880 B2 | 3/2005 | Treat et al. | |
| 6,887,240 B1 | 5/2005 | Lands et al. | |
| 6,889,116 B2 | 5/2005 | Jinno | |
| 6,914,201 B2 | 7/2005 | Van Vooren et al. | |
| 6,926,716 B2 | 8/2005 | Baker et al. | |
| 6,929,644 B2 | 8/2005 | Truckai et al. | |
| 6,932,816 B2 | 8/2005 | Phan | |
| 6,934,134 B2 | 8/2005 | Mori et al. | |
| 6,936,061 B2 | 8/2005 | Sasaki | |
| 8,932,810 | 8/2005 | Ryan | |
| D509,297 S | 9/2005 | Wells | |
| 6,942,662 B2 | 9/2005 | Goble et al. | |
| 6,943,311 B2 | 9/2005 | Miyako | |
| 6,953,430 B2 | 10/2005 | Kidooka | |
| 6,953,461 B2 | 10/2005 | McClurken et al. | |
| 6,958,070 B2 | 10/2005 | Witt et al. | |
| 6,960,210 B2 | 11/2005 | Lands et al. | |
| 6,964,662 B2 | 11/2005 | Kidooka | |
| 6,966,907 B2 | 11/2005 | Goble | |
| 6,972,017 B2 | 12/2005 | Smith et al. | |
| 6,977,495 B2 | 12/2005 | Donofrio | |
| 6,979,786 B2 | 12/2005 | Aukland et al. | |
| 6,981,628 B2 | 1/2006 | Wales | |
| 6,987,244 B2 | 1/2006 | Bauer | |
| 6,994,707 B2 | 2/2006 | Ellman et al. | |
| 6,994,709 B2 | 2/2006 | Iida | |
| 6,997,931 B2 | 2/2006 | Sauer et al. | |
| 7,001,381 B2 | 2/2006 | Harano et al. | |
| 7,011,657 B2 | 3/2006 | Truckai et al. | |
| 7,033,354 B2 | 4/2006 | Keppel | |
| 7,033,356 B2 | 4/2006 | Latterell et al. | |
| 7,041,102 B2 | 5/2006 | Truckai et al. | |
| 7,044,948 B2 | 5/2006 | Keppel | |
| 7,052,489 B2 | 5/2006 | Griego et al. | |
| 7,052,496 B2 | 5/2006 | Yamauchi | |
| 7,063,715 B2 | 6/2006 | Onuki et al. | |
| D525,361 S | 7/2006 | Hushka | |
| 7,070,597 B2 | 7/2006 | Truckai et al. | |
| 7,083,618 B2 | 8/2006 | Couture et al. | |
| 7,083,619 B2 | 8/2006 | Truckai et al. | |
| 7,083,620 B2 | 8/2006 | Jahns et al. | |
| 7,087,051 B2 | 8/2006 | Bourne et al. | |
| 7,087,054 B2 | 8/2006 | Truckai et al. | |
| 7,090,673 B2 | 8/2006 | Dycus et al. | |
| 7,090,689 B2 | 8/2006 | Nagase et al. | |
| 7,101,371 B2 | 9/2006 | Dycus et al. | |
| 7,101,372 B2 | 9/2006 | Dycus et al. | |
| 7,101,373 B2 | 9/2006 | Dycus et al. | |
| 7,103,947 B2 | 9/2006 | Sartor et al. | |
| 7,107,124 B2 | 9/2006 | Green | |
| 7,112,199 B2 | 9/2006 | Cosmescu | |
| D531,311 S | 10/2006 | Guerra et al. | |
| 7,115,123 B2 | 10/2006 | Knowlton et al. | |
| 7,118,570 B2 | 10/2006 | Tetzlaff et al. | |
| 7,118,587 B2 | 10/2006 | Dycus et al. | |
| 7,131,860 B2 | 11/2006 | Sartor et al. | |
| 7,131,970 B2 | 11/2006 | Moses et al. | |
| 7,131,971 B2 | 11/2006 | Dycus et al. | |
| 7,135,020 B2 | 11/2006 | Lawes et al. | |
| D533,942 S | 12/2006 | Kerr et al. | |
| 7,145,757 B2 | 12/2006 | Shea et al. | |
| 7,147,638 B2 | 12/2006 | Chapman et al. | |
| 7,150,097 B2 | 12/2006 | Sremcich et al. | |
| 7,150,749 B2 | 12/2006 | Dycus et al. | |
| 7,153,314 B2 | 12/2006 | Laufer et al. | |

| | | | |
|---|---|---|---|
| D535,027 S | 1/2007 | James et al. | |
| 7,156,842 B2 | 1/2007 | Sartor et al. | |
| 7,156,846 B2 | 1/2007 | Dycus et al. | |
| 7,160,298 B2 | 1/2007 | Lawes et al. | |
| 7,160,299 B2 | 1/2007 | Baily | |
| 7,169,146 B2 | 1/2007 | Truckai et al. | |
| 7,179,255 B2 | 2/2007 | Lettice et al. | |
| 7,179,258 B2 | 2/2007 | Buysse et al. | |
| 7,195,631 B2 | 3/2007 | Dumbauld | |
| D541,418 S | 4/2007 | Schechter et al. | |
| 7,207,990 B2 | 4/2007 | Lands et al. | |
| D541,938 S | 5/2007 | Kerr et al | |
| 7,223,264 B2 | 5/2007 | Daniel et al. | |
| 7,223,265 B2 | 5/2007 | Keppel | |
| 7,232,440 B2 | 6/2007 | Dumbauld et al. | |
| 7,241,288 B2 | 7/2007 | Braun | |
| 7,241,296 B2 | 7/2007 | Buysse et al. | |
| 7,244,257 B2 | 7/2007 | Podhajsky et al. | |
| 7,246,734 B2 | 7/2007 | Shelton, IV | |
| 7,248,944 B2 | 7/2007 | Green | |
| 7,252,667 B2 | 8/2007 | Moses et al. | |
| 7,255,697 B2 | 8/2007 | Dycus et al. | |
| 7,267,677 B2 | 9/2007 | Johnson et al. | |
| 7,270,660 B2 | 9/2007 | Ryan | |
| 7,270,664 B2 | 9/2007 | Johnson et al. | |
| 7,276,068 B2 | 10/2007 | Johnson et al. | |
| 7,300,435 B2 | 11/2007 | Wham et al. | |
| 7,303,557 B2 | 12/2007 | Wham et al. | |
| 7,311,709 B2 | 12/2007 | Truckai et al. | |
| 7,314,471 B2 | 1/2008 | Holman | |
| 7,318,823 B2 | 1/2008 | Sharps et al. | |
| 7,329,256 B2 | 2/2008 | Johnson et al. | |
| 7,329,257 B2 | 2/2008 | Kanehira et al. | |
| D564,662 S | 3/2008 | Moses et al. | |
| 7,338,526 B2 | 3/2008 | Steinberg | |
| 7,342,754 B2 | 3/2008 | Fitzgerald et al. | |
| 7,344,268 B2 | 3/2008 | Jigamian | |
| D567,943 S | 4/2008 | Moses et al. | |
| 7,367,976 B2 | 5/2008 | Lawes et al. | |
| 7,377,920 B2 | 5/2008 | Buysse et al. | |
| 7,384,420 B2 | 6/2008 | Dycus et al. | |
| 7,384,421 B2 | 6/2008 | Hushka | |
| 7,396,336 B2 | 7/2008 | Orszulak et al. | |
| D575,395 S | 8/2008 | Hushka | |
| D575,401 S | 8/2008 | Hixson et al. | |
| 7,435,249 B2 | 10/2008 | Buysse et al. | |
| 7,442,193 B2 | 10/2008 | Shields et al. | |
| 7,442,194 B2 | 10/2008 | Dumbauld et al. | |
| 7,445,621 B2 | 11/2008 | Dumbauld et al. | |
| 7,458,972 B2 | 12/2008 | Keppel | |
| 7,473,253 B2 | 1/2009 | Dycus et al. | |
| 7,481,810 B2 | 1/2009 | Dumbauld et al. | |
| 7,487,780 B2 | 2/2009 | Hooven | |
| 7,491,201 B2 | 2/2009 | Shields et al. | |
| 7,491,202 B2 | 2/2009 | Odom et al. | |
| 7,500,975 B2 | 3/2009 | Cunningham et al. | |
| 7,510,556 B2 | 3/2009 | Nguyen et al. | |
| 7,513,898 B2 | 4/2009 | Johnson et al. | |
| 7,540,872 B2 | 6/2009 | Schechter et al. | |
| 7,549,995 B2 | 6/2009 | Schultz | |
| 7,553,312 B2 | 6/2009 | Tetzlaff et al. | |
| 2002/0013583 A1 | 1/2002 | Camran et al. | |
| 2002/0049442 A1 | 4/2002 | Roberts et al. | |
| 2002/0099372 A1 | 7/2002 | Schulze et al. | |
| 2002/0107517 A1 | 8/2002 | Witt et al. | |
| 2002/0111624 A1 | 8/2002 | Witt et al. | |
| 2002/0188294 A1 | 12/2002 | Couture et al. | |
| 2003/0014052 A1 | 1/2003 | Buysse et al. | |
| 2003/0014053 A1 | 1/2003 | Nguyen et al. | |
| 2003/0018331 A1 | 1/2003 | Dycus et al. | |
| 2003/0018332 A1 | 1/2003 | Schmaltz et al. | |
| 2003/0032956 A1 | 2/2003 | Lands et al. | |
| 2003/0069570 A1 | 4/2003 | Witzel et al. | |
| 2003/0069571 A1 | 4/2003 | Treat et al. | |
| 2003/0078578 A1 | 4/2003 | Truckai et al. | |
| 2003/0109875 A1 | 6/2003 | Tetzlaff et al. | |
| 2003/0114851 A1 | 6/2003 | Truckai et al. | |
| 2003/0130653 A1* | 7/2003 | Sixto et al. ............ 606/45 | |
| 2003/0139741 A1 | 7/2003 | Goble et al. | |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0148035 A1 | 7/2004 | Barrett et al. |
| 2004/0162557 A1 | 8/2004 | Tetzlaff et al. |
| 2004/0176762 A1 | 9/2004 | Lawes et al. |
| 2004/0193153 A1 | 9/2004 | Sartor et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0225288 A1 | 11/2004 | Buysse et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter, III et al. |
| 2005/0004564 A1 | 1/2005 | Wham et al. |
| 2005/0004568 A1 | 1/2005 | Lawes et al. |
| 2005/0004569 A1 | 1/2005 | Witt et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |

| | | |
|---|---|---|
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0364216 A1 | 4/1990 |
| EP | 0467501 | 1/1992 |
| EP | 518230 A1 | 12/1992 |
| EP | 0 541 930 B1 | 5/1993 |
| EP | 0572131 | 12/1993 |
| EP | 584787 A1 | 3/1994 |
| EP | 0589453 A2 | 3/1994 |
| EP | 0589555 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 0517243 | 9/1997 |
| EP | 853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1177771 | 2/2002 |
| EP | 1301135 A | 4/2003 |
| EP | 1330991 A1 | 7/2003 |
| EP | 1486177 A2 | 6/2004 |
| EP | 1472984 A1 | 11/2004 |
| EP | 0774232 | 1/2005 |
| EP | 1527747 A2 | 5/2005 |
| EP | 1530952 A1 | 5/2005 |

| | | |
|---|---|---|
| EP | 1532932 A1 | 5/2005 |
| EP | 1535581 A2 | 6/2005 |
| EP | 1609430 A1 | 12/2005 |
| EP | 1632192 A1 | 3/2006 |
| EP | 1642543 | 4/2006 |
| EP | 1645238 A1 | 4/2006 |
| EP | 1645240 A2 | 4/2006 |
| EP | 1649821 | 4/2006 |
| EP | 1707143 A1 | 10/2006 |
| EP | 1769765 | 4/2007 |
| EP | 1769766 | 4/2007 |
| EP | 1929970 | 6/2008 |
| EP | 1683496 | 12/2008 |
| GB | 623316 | 5/1949 |
| GB | 1490585 | 11/1977 |
| GB | 2214430 A | 6/1989 |
| GB | 2213416 | 8/1989 |
| JP | 501068 | 9/1984 |
| JP | 502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 | 11/1974 |
| WO | WO89/00757 | 1/1989 |
| WO | WO 92/04873 | 4/1992 |
| WO | WO 92/06642 | 4/1992 |
| WO | WO 93/21845 | 11/1993 |
| WO | WO 94/08524 A | 4/1994 |
| WO | WO94/20025 | 9/1994 |
| WO | WO 95/02369 | 1/1995 |
| WO | WO95/07662 | 3/1995 |
| WO | WO 95/07662 | 3/1995 |
| WO | WO95/15124 | 6/1995 |
| WO | WO96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO97/10764 | 3/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 A | 12/1999 |
| WO | WO 00/24330 | 5/2000 |
| WO | WO00/24331 | 5/2000 |
| WO | WO 00/24331 | 5/2000 |
| WO | WO 00/36986 | 6/2000 |
| WO | WO 00/41638 | 7/2000 |
| WO | WO00/47124 | 8/2000 |
| WO | WO 00/53112 | 9/2000 |
| WO | WO 01/17448 A | 3/2001 |
| WO | WO 01/54604 | 8/2001 |
| WO | WO02/07627 | 1/2002 |
| WO | WO 02/07627 | 1/2002 |
| WO | WO 02/067798 A1 | 9/2002 |
| WO | WO02/080783 | 10/2002 |
| WO | WO 02/080783 | 10/2002 |
| WO | WO02/080784 | 10/2002 |
| WO | WO 02/080784 | 10/2002 |
| WO | WO02/080785 | 10/2002 |
| WO | WO 02/080785 | 10/2002 |
| WO | WO02/080786 | 10/2002 |
| WO | WO 02/080786 | 10/2002 |
| WO | WO02/080793 | 10/2002 |
| WO | WO 02/080793 | 10/2002 |
| WO | WO02/080794 | 10/2002 |
| WO | WO 02/080794 | 10/2002 |
| WO | WO 02/080795 | 10/2002 |
| WO | WO 02/080796 | 10/2002 |
| WO | WO02/080797 | 10/2002 |
| WO | WO 02/080797 | 10/2002 |
| WO | WO 02/080798 | 10/2002 |
| WO | WO 02/080799 | 10/2002 |
| WO | WO02/081170 | 10/2002 |
| WO | WO 02/081170 | 10/2002 |
| WO | WO 03/061500 | 7/2003 |
| WO | WO 03/090630 A3 | 11/2003 |
| WO | WO 03/101311 | 12/2003 |
| WO | WO 2004/032776 A1 | 4/2004 |
| WO | WO2004/032777 | 4/2004 |
| WO | WO 2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO2004/073490 | 9/2004 |
| WO | WO2004/073753 | 9/2004 |
| WO | WO 2004/082495 | 9/2004 |
| WO | WO 2004/098383 | 11/2004 |
| WO | WO 2004/103156 | 12/2004 |
| WO | 2005/004734 A1 | 1/2005 |
| WO | WO2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Sigel et al "The Mechanism of Blood Vessel Closure by High Frequency Electrocoagulation" Surgery Gynecology & Obstetrics, Oct. 1965 pp. 823-831.
Bergdahl et al "Studies on Coagulation and the Development of an Automatic Computerized Bipolar Coagulator" J.Neurosurg, vol. 75. Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al "A Phase I Study of the LigaSure Vessel Sealing System in Hepatic Surgery" Section of HPB Surger. Washington University School of Medicine, St. Louis MO, Presented at AHPBA, Feb. 2001.

Johnson et al "Evaluation of the LigaSure Vessel Sealing System in Hemorrhoidectormy" American College of Surgeons (ACS) Clinicla Congress Poster (2000).
Sayfan et al "Sutureless Closed Hemorrhoidectomy: A New Technique" Annals of Surgery vol. 234 No. 1 Jul. 2001 pp. 21-24.
Heniford et al "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Levy et al, "Use of a New Energy-based Vessel Ligation Device During Vaginal Hysterectomy" Int'l Federation of Gynecology and Obstetrics (FIGO) World Congress 1999.
Crawford et al "Use of the LigaSure Vessel Sealing System in Urologic Cancer Surger" Grand Rounds in Urology 1999 vol. 1 Issue 4 pp. 10-17.
Rothenberg et al "Use of the LigaSure Vessel Sealing System in Minimally Invasive Surgery in Children" Int'l Pediatric Endosurgery Group (IPEG) 2000.
Palazzo et al "Randomized clinical trial of Ligasuro versus open haemorrhoidectomy" British Journal of Surgery 2002, 89, 154-157.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Carbonell et al. "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.
"Reducing Needlestick Injuries in the Operating Room" Sales/Product Literature 2001.
Chung et al . "Clinical Experience of Sutureless Closed Hemorrhoidectomy with LigaSure" Diseases of the Colon & Rectum vol. 46, No. 1 Jan. 2003.
Strasberg et al , "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G Horgan, "A Novel Technique for Parenchymal Division During Hepatectomy" The American Journal of Surgery, vol. 181, No. 3, Apr. 2001 pp. 236-237.
W Scott Helton, "LigaSure Vessel Sealing System: Revolutionary Hemostasis Product for General Surgery"Sales/Product Literature 1999.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al.. "Initial Experience With the LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al , "Update on Hysterectomy—New Technologies and Techniques" OBG Management, Feb. 2003.
Barbara Levy. "Use of a New Vessel Ligation Device During Vaginal Hysterectomy" FIGO 2000, Washington, D.C.
McLellan et al "Vessel Sealing for Hemostasis During Gynecologic Surgery" Sales/Product Literature 1999.
Sengupta et al , "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
E David Crawford "Use of a Novel Vessel Sealing Technology in Management of the Dorsal Veinous Complex" Sales/Product Literature 2000.
Jarrett et al , "Use of the LigaSure Vessel Sealing System for Peri-Hilar Vessels in Laparoscopic Nephrectomy" Sales/Product Literature 2000.
E David Crawford "Evaluation of a New Vessel Sealing Device in Urologic Cancer Surgery" Sales/Product Literature 2000.
Joseph Ortenberg "LigaSure System Used in Laparoscopic 1st and 2nd Stage Orchiopexy" Innovations That Work, Nov. 2002.
Koyle et al , "Laparoscopic Palomo Varicocele Ligation in Children and Adolescents" Pediatric Endosurgory & Innovative Techniques, vol. 6. No. 1, 2002.
Dulemba et al "Use of a Bipolar Electrothermal Vessel Sealer in Laparoscopically Assisted Vaginal Hysterectomy" Sales/Product Literature, Jan. 2004.
Johnson et al. "Evaluation of a Bipolar electrothermal Vessel Sealing Device in Hemorrhoidectomy" Sales/Product Literature; Jan. 2004.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.
Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

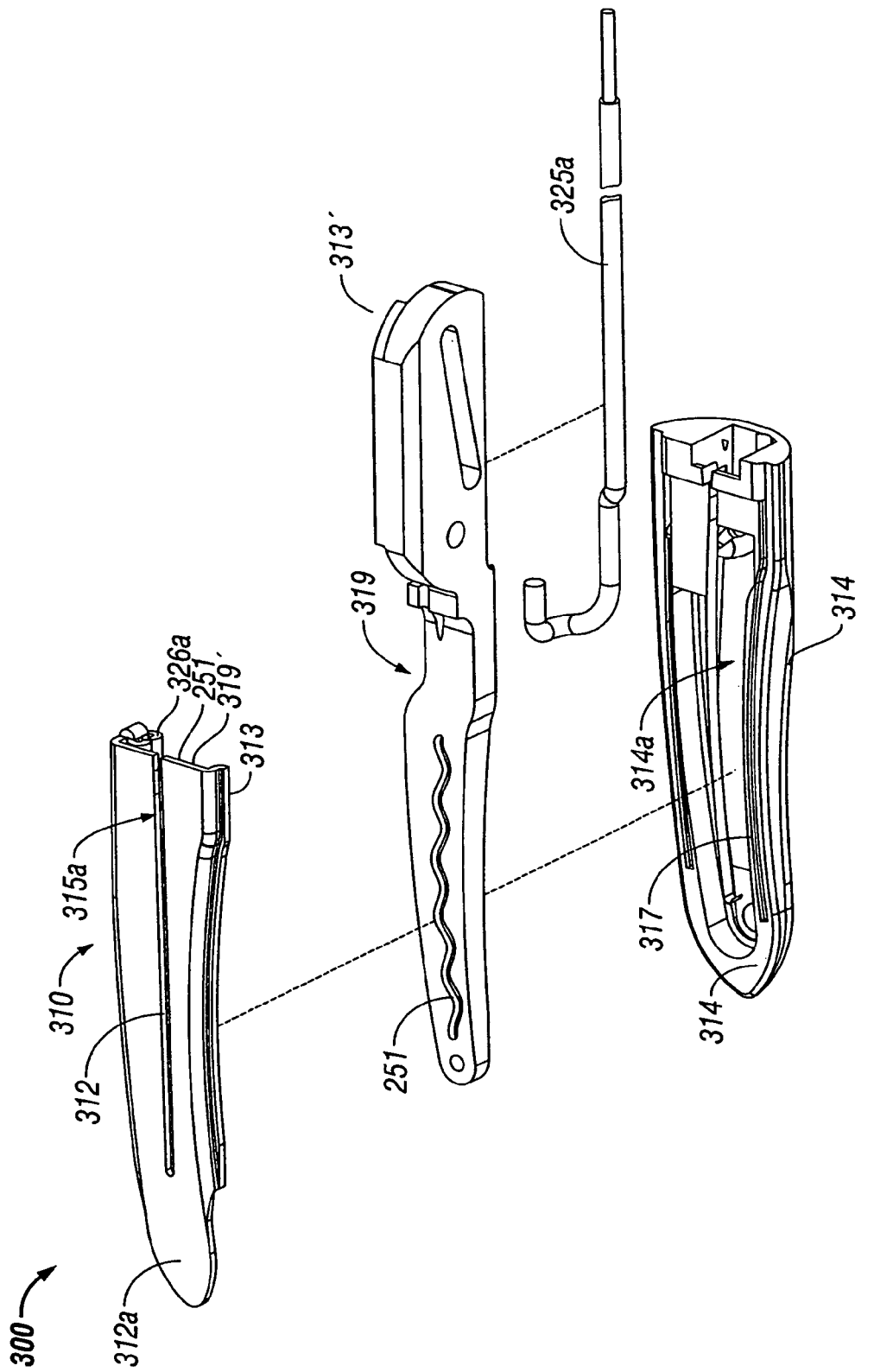

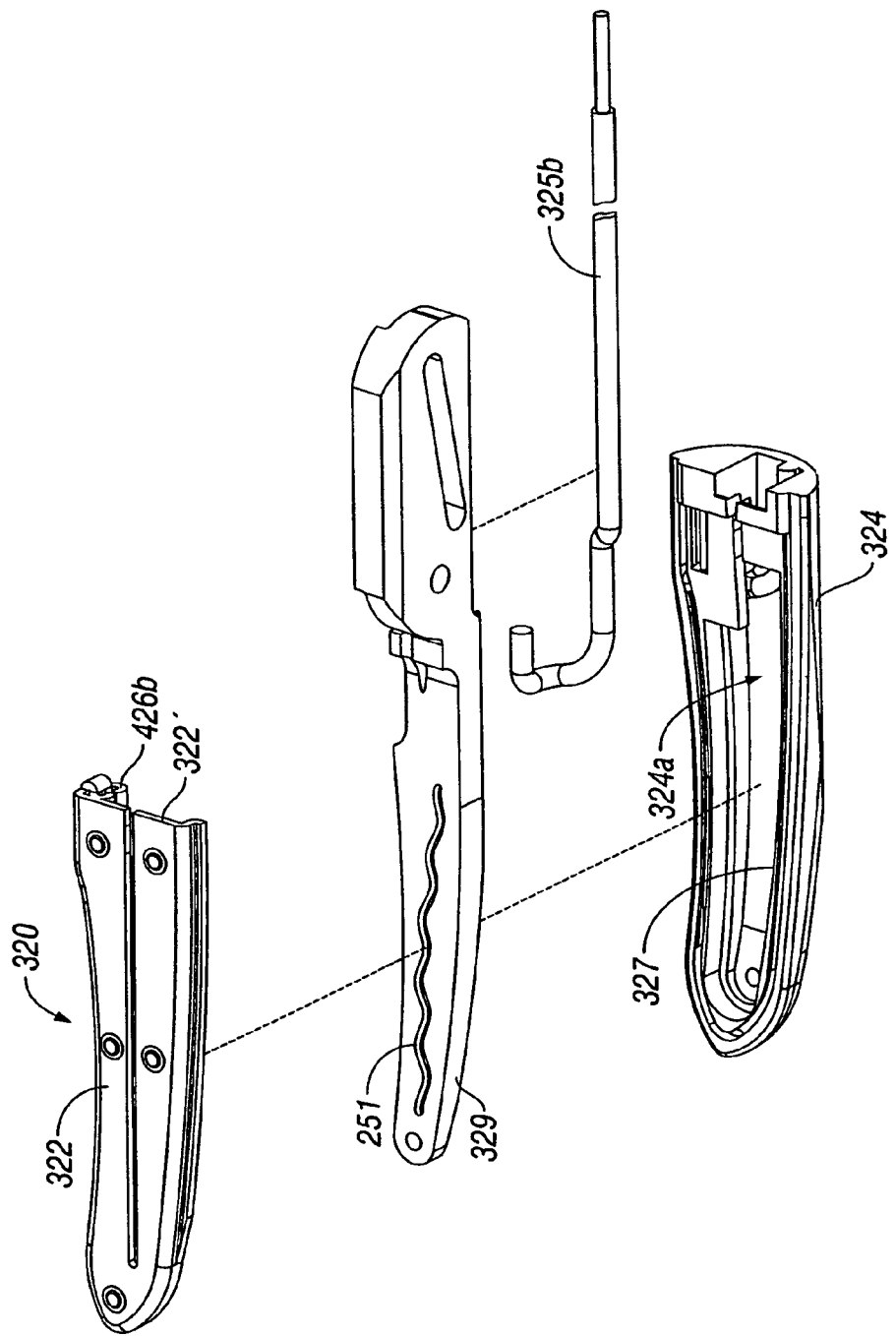

METHOD FOR MANUFACTURING AN END EFFECTOR ASSEMBLY

CROSS-REFERENCE TO RELATED APPLICATIONS

This application claims the benefit of priority of U.S. Provisional Patent Application Ser. No. 60/722,186 by Paul Guerra entitled "METHOD FOR MANUFACTURING AN END EFFECTOR ASSEMBLY" filed on Sep. 30, 2005, the entire contents of which is incorporated herein by reference.

BACKGROUND

The present disclosure relates to electrosurgical instruments used for open and endoscopic surgical procedures. More particularly, the present disclosure relates to a method of manufacturing a bipolar forceps for sealing vessels and vascular tissue having an electrode assembly that is designed to enhance electrical isolation of the surface of the jaw of the forceps from an underlying strength member.

TECHNICAL FIELD

A hemostat or forceps is a simple plier-like tool that uses mechanical action between its jaws to constrict tissue and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

By utilizing an electrosurgical forceps, a surgeon can either cauterize, coagulate/desiccate tissue and/or simply reduce or slow bleeding by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad that is attached externally to the patient. When the electrosurgical energy is applied, the energy travels from the active electrode, to the surgical site, through the patient and to the return electrode.

Bipolar electrosurgical forceps utilize two generally opposing electrodes that are generally disposed on the inner facing or opposing surfaces of the end effectors, which are, in turn, electrically coupled to an electrosurgical generator. Each electrode is charged to a different electric potential. Since tissue is a conductor of electrical energy, when the end effectors are utilized to clamp or grasp tissue therebetween, the electrical energy can be selectively transferred through the tissue.

Over the last several decades, more and more surgeons are complimenting traditional open methods of gaining access to vital organs and body cavities with endoscopes and endoscopic instruments that access organs through small puncture-like incisions. Endoscopic instruments are inserted into the patient through a cannula, or port, that has been made with a trocar. Typical sizes for cannulas range from three millimeters to twelve millimeters. Smaller cannulas are usually preferred, which, as can be appreciated, ultimately presents a design challenge to instrument manufacturers who must find ways to make surgical instruments that fit through the cannulas.

Certain surgical procedures require sealing blood vessels or vascular tissue. However, due to space limitations, surgeons can have difficulty suturing vessels or performing other traditional methods of controlling bleeding, e.g., clamping and/or tying-off transected blood vessels. Blood vessels, in the range below two millimeters in diameter, can often be closed using standard electrosurgical techniques. If a larger vessel is severed, it may be necessary for the surgeon to convert the endoscopic procedure into an open-surgical procedure and thereby abandon the benefits of laparoscopy.

It is known that the process of coagulating small vessels is fundamentally different than vessel sealing. For the purposes herein the term "coagulation" is defined as a process of desiccating tissue wherein the tissue cells are ruptured and dried. The term "vessel sealing" is defined as the process of liquefying the collagen in the tissue so that the tissue cross-links and reforms into a fused mass. Thus, coagulation of small vessels is sufficient to close them, however, larger vessels need to be sealed to assure permanent closure.

Several journal articles have disclosed methods for sealing small blood vessels using electrosurgery. An article entitled *Studies on Coagulation and the Development of an Automatic Computerized Bipolar Coagulator*, Journal of Neurosurgery, Volume 75, July 1991, describes a bipolar coagulator that is used to seal small blood vessels. The article states that it is not possible to safely coagulate arteries with a diameter larger than 2 to 2.5 mm. A second article is entitled *Automatically Controlled Bipolar Electrocoagulation—"COA-COMP"*, Neurosurg. Rev. (1984), pp. 187-190, describes a method for terminating electrosurgical power to the vessel so that charring of the vessel walls can be avoided.

In order to effect a proper seal with larger vessels, two predominant mechanical parameters must be accurately controlled—the pressure applied to the vessel and the gap between the electrodes, both of which affect thickness of the sealed vessel. More particularly, accurate application of the pressure may be important for several reasons: 1) to oppose the walls of the vessel; 2) to reduce the tissue impedance to a low enough value that allows enough electrosurgical energy through the tissue; 3) to overcome the forces of expansion during tissue heating; and 4) to contribute to the end tissue thickness, which is an indication of a good seal. In some instances a fused vessel wall is optimum between 0.001 and 0.006 inches. Below this range, the seal may shred or tear and above this range the lumens may not be properly or effectively sealed.

Numerous bipolar electrosurgical instruments have been proposed in the past for various open and endoscopic surgical procedures. However, some of these designs may not provide uniformly reproducible pressure to the blood vessel and may result in an ineffective or non-uniform seal. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, sealing and cutting vessels or tissue.

Many of these instruments include blade members or shearing members that simply cut tissue in a mechanical and/or electromechanical manner and are relatively ineffective for vessel sealing purposes. Other instruments generally rely on clamping pressure alone to procure proper sealing thickness and are often not designed to take into account gap tolerances and/or parallelism and flatness requirements, which are parameters that, if properly controlled, can assure a consistent and effective tissue seal. For example, it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

Currently, several tissue sealing devices employ jaws that are designed as two separate parts. The jaw is first covered in an over-mold material. Then the seal plate and the covered jaw are over-molded together. As a result, this manufacturing process requires two mold tools. In addition, each part must include features by which the part can be held while the molding occurs.

SUMMARY

It is an object of the present disclosure to provide a method for manufacturing an open and/or endoscopic electrosurgical instrument in which the two separate parts of the jaws of the forceps can be molded simultaneously to save tooling costs by first disposing an insulating layer on the back of the seal plate.

It is another object of the present disclosure to provide an open and/or endoscopic electrosurgical instrument in which the covering or coating on the back of the seal plate has enhanced thermal and electrical properties for isolation as compared to the thermal and electrical properties of the plastic mold material.

More particularly, one embodiment of the present disclosure relates to a method of manufacturing a jaw member of an end effector assembly for use with an electrosurgical instrument. The method includes the steps of providing an electrically conductive tissue engaging plate and a jaw support; covering one side of the electrically conductive tissue engaging plate with an electrically insulative, thermally non-degrading coating; placing and securing the electrically conductive tissue engaging plate and the jaw support into a jaw mold; and introducing a liquid substance into the jaw mold and allowing the liquid substance to cure around the electrically conductive tissue engaging plate and the jaw support. The coating of the covering step may be of uniform thickness across the electrically conductive tissue engaging plate. In addition, the coating of the covering step may include a thickness which provides a gap-set between the electrically conductive tissue engaging plate and the jaw support during the introducing step.

One embodiment of the present disclosure relates to another method for manufacturing a jaw member of an end effector assembly for use with an electrosurgical instrument wherein the method includes the steps of: providing an electrically conductive tissue engaging plate and a jaw support; covering one side of the electrically conductive tissue engaging plate with an electrically insulative, thermally non-degrading coating; and securing the side of the electrically conductive tissue engaging plate onto the jaw support with an adhesive. The coating of the covering step may be of uniform thickness across the electrically conductive tissue engaging plate. The coating of the covering step may include a thickness which provides a gap-set between the electrically conductive tissue engaging plate and the jaw support during the introducing step.

BRIEF DESCRIPTION OF THE DRAWINGS

FIG. 2A is a greatly-enlarged, top perspective view of a bottom jaw member of an end effector assembly with parts separated having an insulating layer applied according to one embodiment of the present disclosure;

FIG. 3A is a greatly-enlarged, top perspective view of a top jaw member of an end effector assembly with parts separated having an insulating layer applied according to one embodiment of the present disclosure;

DETAILED DESCRIPTION

It has been found that by altering the configuration of the electrode insulating material relative to the electrically conductive sealing surface, surgeons can more readily and easily produce a consistent, high quality seal and effectively reduce thermal spread across or to adjacent tissue. For the purposes herein the term "thermal spread" refers generally to the heat transfer (heat conduction, heat convection or electrical current dissipation) dissipating along the periphery of the electrically conductive or electrically active surfaces to adjacent tissue. This can also be termed "collateral damage" to adjacent tissue. It is envisioned that the configuration of the insulating material that surrounds the perimeter of the electrically conductive surface will effectively reduce current and thermal dissipation to adjacent tissue areas and generally restrict current travel to areas between the opposing electrodes. As mentioned above, this is different from dielectrically coating the outer surfaces of the instrument to prevent tissue "blanching" at points normal to the sealing site. These coatings are not designed or intended to reduce collateral tissue damage or thermal spread to adjacent tissue (tissue lying along the tissue sealing plane).

More particularly, altering the geometrical dimensions of the insulator relative to the electrically conductive surface alters the electrical path, thereby influencing the thermal spread/collateral damage to adjacent tissue structures. Preferably, the geometry of the insulating substrate also isolates the two electrically opposing poles (i.e., electrodes) from one another, thereby reducing the possibility that tissue or tissue fluids can create an unintended bridge or path for current travel. In other words, the insulator and electrically conductive sealing surface are preferably dimensioned such that the current is concentrated at the intended sealing site between the opposing electrically conductive surfaces as explained in more detail below.

Figure 1:
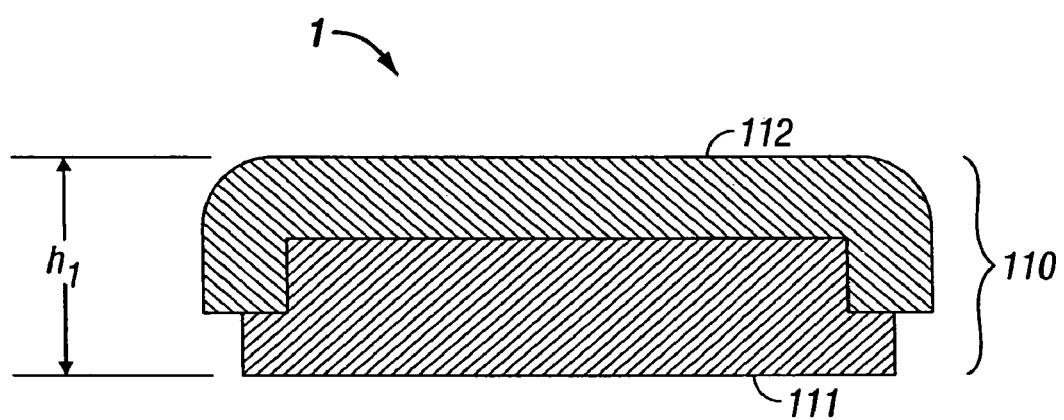
FIG. 1 is a cross-section of a prior art electrode configuration with the electrode extending over the sides of the insulator.

Referring now to FIG. 1, an electrode jaw member 110 of an end effector assembly of the prior art is shown in which an electrically conductive seal surface 112 is disposed on an electrically insulating layer 111. The electrically conductive seal surface 112 contacts tissue. The electrically conductive seal surface 112 has a width such that the electrically conductive seal surface 112 overlaps the electrically insulating layer 111. The joining process of the electrically conductive seal surface 112 and the electrically insulating layer 111 result in electrode jaw member 110 having a height "h1".

With respect to the method of manufacturing electrode jaw member 110, the jaw member 110 is first covered in an over-mold material and then the seal plate 112 and covered jaw 112 are over-molded together. The process requires two mold tools and features on each part to be held while the molding occurs.

Figure 2B:
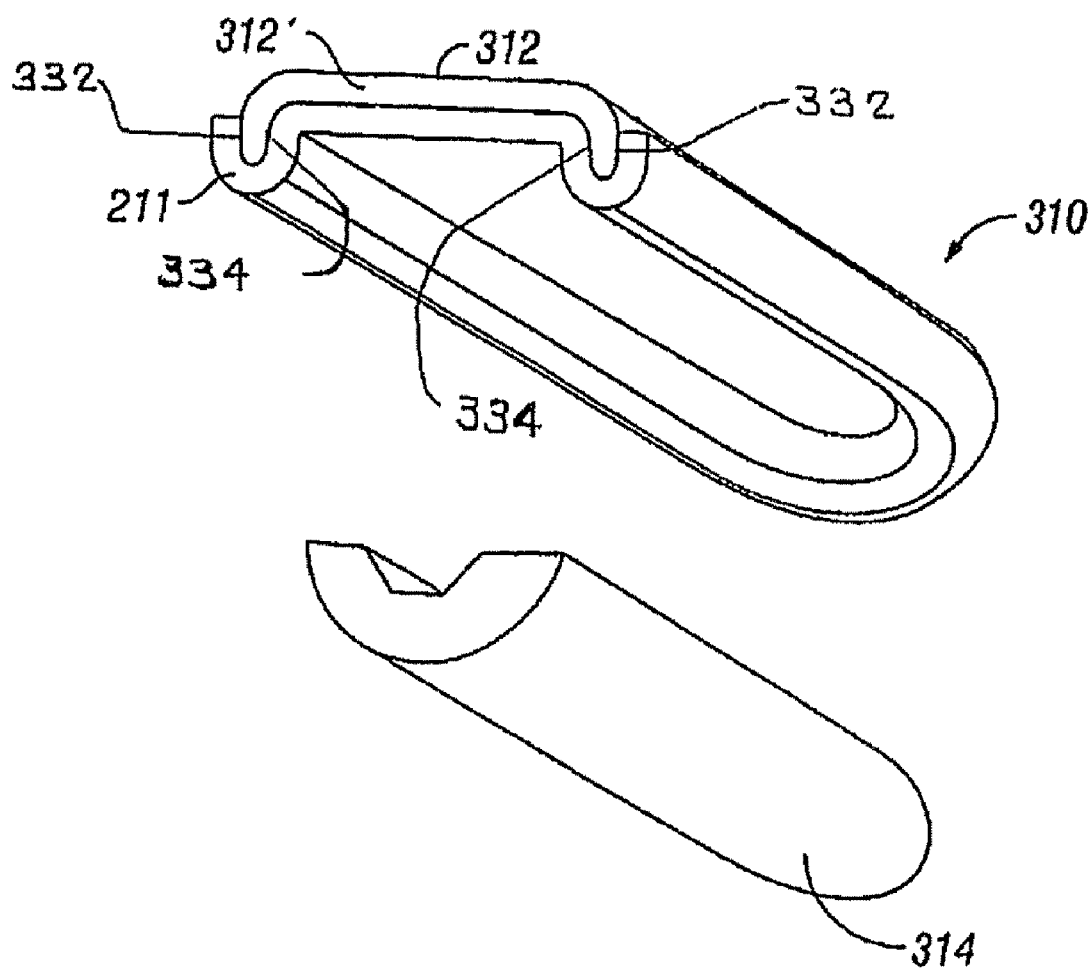
FIG. 2B is a greatly-enlarged, bottom perspective view of the bottom jaw member of an end effector assembly of FIG. 2A.

Referring to FIGS. 2A, 2B, 3A and 3B, in one embodiment of the present disclosure, as best shown in FIG. 2A, a jaw member 310 of an electrosurgical forceps may include a support base 319 which extends distally from a flange 313. The jaw member 310 includes an electrically conductive tissue engaging surface or sealing plate 312. As best shown in FIG. 2B, the electrically conductive tissue engaging sealing plate 312 has vertically-extending edges 332, 334 extending about a periphery and along a length thereof of the electrically conductive plate 312. Vertically-extending edges 332 extend externally along the electrically conductive tissue engaging surface or sealing plate 312 while vertically-extending edges 334 extend internally along an opposite side surface 312' of the electrically conductive tissue engaging surface or sealing plate 312. An electrically insulating layer 211 is disposed on the opposite side surface 312' and along the vertically-extending edges 334 that extend internally along the opposite side surface 312' and along at least a portion of the vertically-extending edges 332 that extend externally along the electrically conductive tissue engaging surface or sealing plate 312. A jaw support base 319 together with the electrically insulating layer 211 and electrically conductive tissue engaging surface 312 are encapsulated by an outer insulative housing or overmolding 314. Overmolding 314 includes a cavity 314a is dimensioned to securely engage the electrically conductive sealing surface or sealing plate 312 as well as the support base 319 and electrically insulating layer 211. Consequently, jaw member 310 has an electrically conductive sealing surface or sealing plate member 312 that is substantially surrounded by electrically insulating layer 211 and outer insulative housing or overmolding 314. The electrically conductive seal surface 312 contacts tissue.

For example, and as shown in FIG. 2A, the electrically conductive sealing plate 312 includes a peripheral flange 313, which surrounds the periphery of the sealing plate 312.

Figure 4:
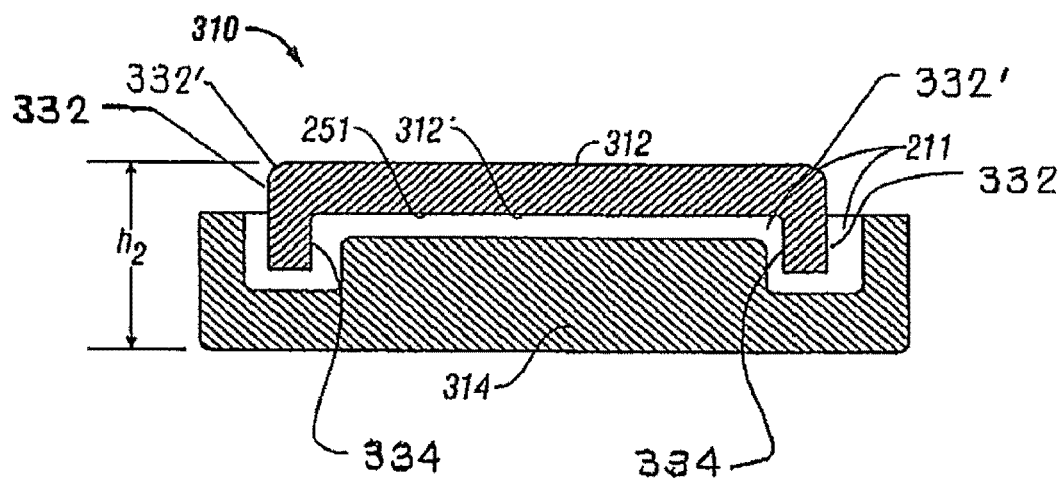
FIG. 4 is a cross-section of the electrode with an insulating layer applied to the electrode of FIGS. 2A and 2B.

Flange 313, is designed to matingly engage an inner lip 317 of the outer insulative housing or overmolding 314. A lead 325a extending from a circuit board (not shown) terminates within the outer insulating housing or overmolding 314 and is designed to electro-mechanically couple to the sealing plate 312 by virtue of a crimp-like connection 326a. For example, the electrically insulating layer 211 is disposed on the opposite side surface 312' and along the vertically-extending edges 334 that extend internally along the opposite side surface 312' and along at least a portion of the vertically-extending edges 332 that extend externally along the electrically conductive tissue engaging surface or sealing plate 312, electrically conductive sealing surface 312 and the outer insulating housing or overmolding 314 are preferably dimensioned to limit and/or reduce many of the known undesirable effects related to tissue sealing, e.g., flashover, thermal spread and stray current dissipation As best shown in FIG. 4, electrically conductive sealing surface 312 may also include outer peripheral edges 332' that have a pre-defined radius and the outer insulating housing or overmolding 314 meets the electrically insulating layer 211 and the electrically conductive sealing surface 312 along an adjoining edge 332 of the sealing surface 312 in a generally tangential position. At the interface, the electrically conductive surface 312 is raised relative to the outer housing 314.

Figure 3B:
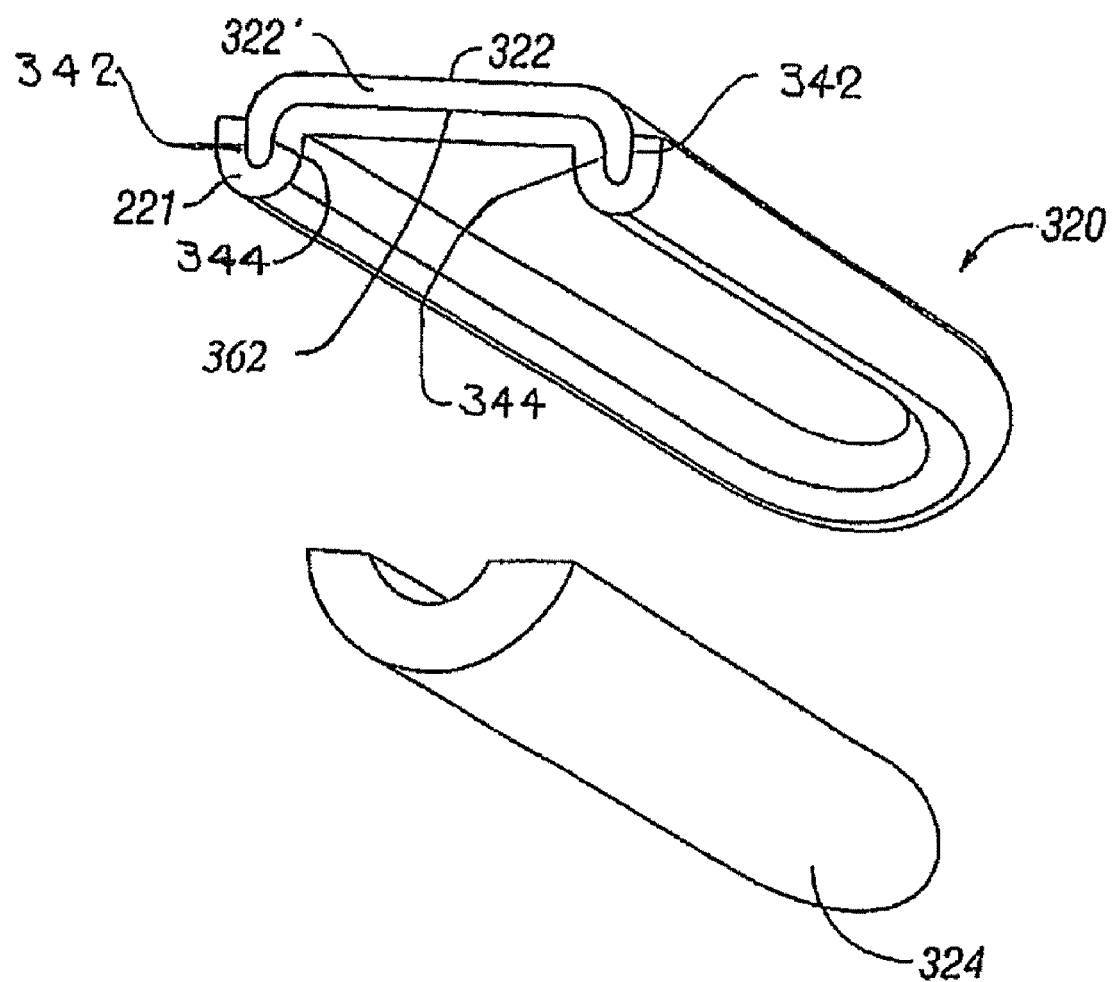
FIG. 3B is a greatly-enlarged, bottom perspective view of the jaw member of an end effector assembly of FIG. 3A.

As best illustrated in FIGS. 3A and 3B, jaw member 320 includes similar elements to jaw member 310 such as jaw insulating housing or overmolding 324, that encapsulates a support plate 329, an electrically insulating layer 221 and an electrically conductive tissue engaging sealing surface or sealing plate member 322. Similarly, the electrically conductive tissue engaging sealing plate 322 has vertically-extending edges 342, 344 extending about the periphery and along a length thereof of the electrically conductive plate 322. Vertically-extending edges 342 extend externally along the electrically conductive tissue engaging surface or sealing plate 322 while vertically-extending edges 344 extend internally along an opposite side surface 322' of the electrically conductive tissue engaging surface or sealing plate 322. The electrically conductive surface or sealing plate member 322 forms a channel 362 on the opposite side surface 322' of electrically conductive surface or sealing plate 322 such that the electrically conductive surface or sealing plate 322 and the channel 362 are dimensioned for the channel 362 to receive electrically insulating layer 221 disposed on the opposite side surface 322'.

Jaw member 320 may be assembled in a similar manner as described above with respect to jaw member 310, as described below.

Jaw members 310 and 320 are electrically isolated from one another such that electrosurgical energy can be effectively transferred through the tissue to form a tissue seal. For example, each jaw member, e.g., 310, includes a uniquely-designed electrosurgical cable path disposed therethrough that transmits electrosurgical energy to the electrically conductive sealing surface 312. Cable leads 325a and 325b, which supply power to electrode jaw members 310 and 320, respectively, are coupled to an electrosurgical generator (not shown) and are supported via support plates 319 and 329, respectively, and are held loosely but securely along the cable path to permit rotation of the jaw members 310 and 320. This configuration isolates electrically conductive sealing surface 312 from the remaining operative components of the end effector assembly 1000 or 122, jaw member 320 and shaft 12 or 109 (see FIGS. 6 and 7) and conversely isolates electrically conductive sealing surface 322 from the remaining operative components of the jaw member 310. The two electrical potentials are isolated from one another by virtue of the insulative sheathing surrounding the cable leads 325a and 325b.

FIG. 4 shows, in one embodiment, that the electrically insulating layer 211 or 221 may be made from a polymer or a polymer solution, which can be sprayed onto the opposite sides 312' and 322' of the conductive sealing surface 312 and 322, respectively. Alternatively, a ceramic material may be applied to the opposite sides 312' and 322' of electrically conductive seal plates or sealing surfaces 312 and 322 by plasma deposition or by other suitable mechanical techniques. The electrically insulating layers 211 and 221 may also be sprayed on in a uniform thickness to assure flatness.

By applying a coating of electrically insulating layer 211 and 221 onto sides 312' and 322' and vertically extending edges 332, 334 and 342, 344 of electrically conductive seal plates 312 and 322, respectively, enhanced thermal and electrical properties are provided so as to increase electrical and thermal isolation during activation, and may be dimensioned to regulate the gap distance to within a preferred gap range as described in more detail below with respect to FIG. 6. The coating of electrically insulating layer 211 and 221 may be made from a material selected from the group consisting of flame sprayed ceramic, vapor deposition polymer (parylene), an oxide layer, and an anodized coating.

In one particularly useful embodiment, overmoldings 314 and 324 are made from molded plastic material.

Figure 5:
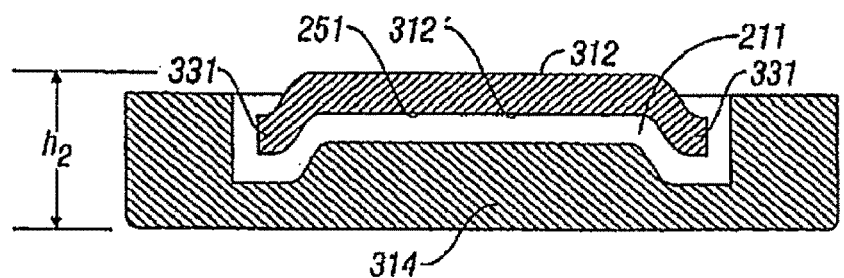
FIG. 5 is a cross-section of an overmolded stamped electrode configuration showing an insulating layer applied to the electrode of FIGS. 2A and 2B and capturing a pinch trim which depends from the electrically conductive surface.

In another particularly useful embodiment, as best illustrated in FIGS. 2, 3 and 5, the insulating layer 211 of electrode 310 is attached to seal surface 312' by applying an adhesive in an adhesive layer 251. The adhesive layer 251 may include a material that includes polyurethane or other adhesive fluids. In this case, the application of the jaw overmolding 314 is applied over the insulating layer 211 is optional. Those skilled in the art will recognize that adhesive 251 may be applied in a similar manner to the insulating layer 221 of electrode 320 and seal surface 322'. The method of manufacturing the insulating layer 211 or 221 using adhesive 251 is described below.

Figure 6:
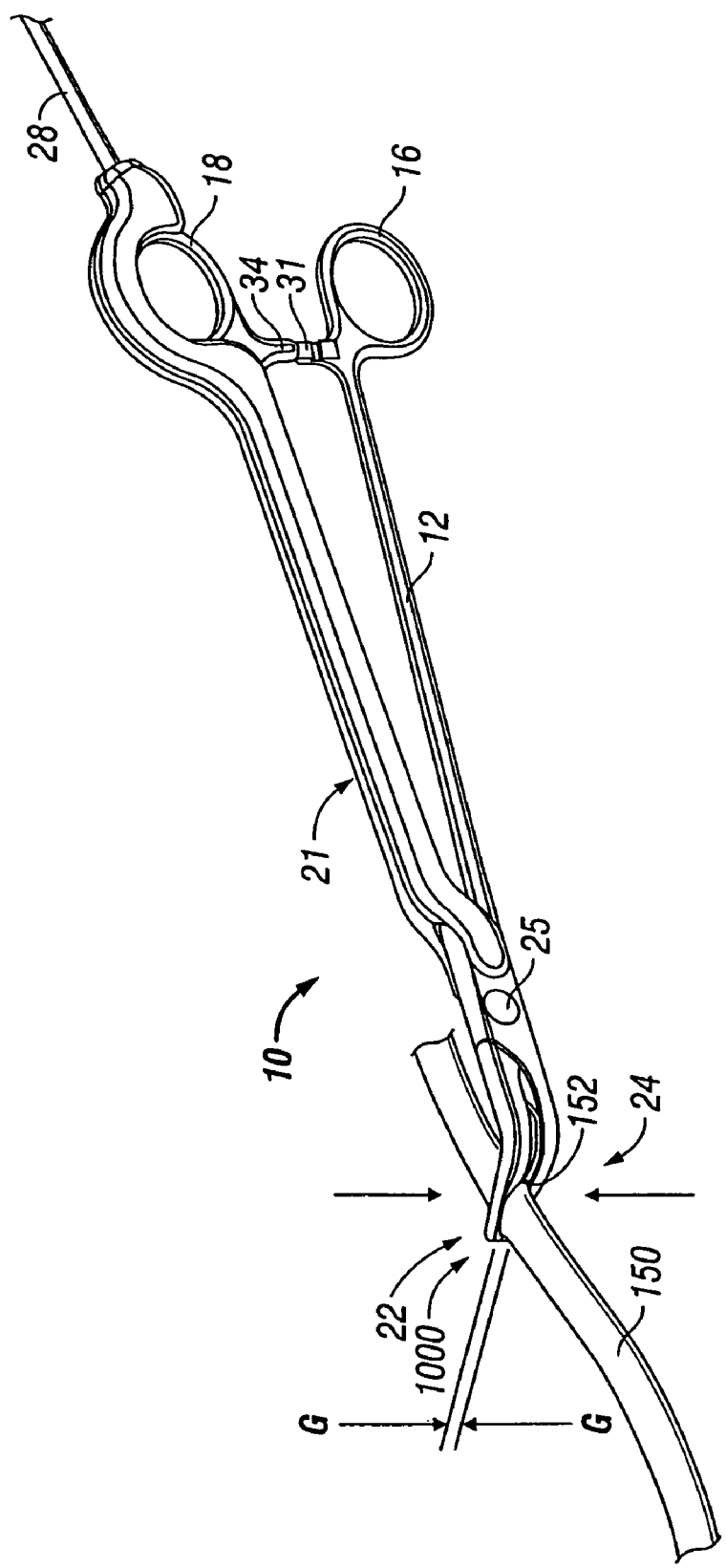
FIG. 6 is a perspective view of the open forceps of the present disclosure showing the operative motion of the forceps to effect sealing of a tubular vessel.

As mentioned above, the electrically insulating layers 211 and 221 and the overmolding 314 and 324 not only insulate the electric current but may also be dimensioned to regulate the gap distance G between the electrodes 310 and 320 when closed about tissue, which is known to contribute to the seal quality, consistency and the reduction of thermal spread across the tissue (See FIG. 6). Specifically, the coating regulates the gap set between the jaw support 319 or 329 and the plate 312 or 322 when inserted into the mold, The jaw mechanism (i.e., jaw members 310 and 320) and the coated seal surfaces 312 and 322 are held together simultaneously in a mold tool while plastic is caused to flow around the jaw members 310 and 320.

In addition, by attaching the electrically insulating layer 211 and 221 and overmolding 314 and 324 to the conductive surfaces 312' and 322', respectively, utilizing one of the above assembly techniques, the alignment and thickness, i.e., height "h2", of the electrodes 310 and 320 can be controlled. For example, and as best illustrated in comparison of FIG. 1 to FIG. 4, the overmolding manufacturing technique reduces the overall height "h2" (FIG. 4) of the electrode 310 compared to traditional manufacturing techniques, which yield a height of "h1" (FIG. 1). The smaller height "h2" allows a user access to smaller areas within the body and facilitates sealing around more delicate tissue areas.

Moreover, the overmolding technique provides more insulation, i.e., electrically Insulative layers 211 and 221, along the vertically extending edges of the electrically conductive surface, which also reduces thermal spread due to less electrode to tissue contact. By dimensioning electrically insulating layer, e.g., 211 and electrode 310 in this fashion (i.e., with reduced conductive surface area), the current is restricted (i.e., concentrated) to the intended seal area rather than current being able to travel to tissue outside the seal area, which may come into contact with an outer edge of the electrode 310 (see FIG. 4). In addition, the material of the jaw overmolding 314 (and 324) provides enhanced thermal and electrical insulation properties during activation.

More particularly, the varying geometry of the electrically insulating layer 211 (and 221) and jaw overmolding 314 (and 324) compared to the electrically conductive surface 312 also isolates the two opposing poles during activation, thereby reducing the possibility that tissue or tissue fluids will bridge a path for stray current being able to travel to surrounding tissue. As best seen in FIGS. 3A, 3B, 4 and 5, the electrode 310 may also include a pinch trim 331 that facilitates secure, integral engagement of the electrically insulating layer 211 (and 221) and jaw overmolding 314 (and 324) and the electrically conductive sealing surface 312 during the assembly and/or manufacturing process.

FIG. 6 shows a bipolar forceps 10 having an end effector assembly 1000 during use wherein handle members 16 and 18 are moved closer to one another to apply clamping force to the tubular tissue 150 to effect a seal 152. The end effector assembly 1000 may include first and second electrode jaw members 310 and 320, as previously described. Movement of the handle members 16 and 18 closer to one another is restricted by a gap set "G", which is established between the upper electrically conductive seal plate 312 and the lower electrically conductive seal plate 322 by the application of the electrically insulating seal layers 211 and 221, respectively. Once sealed, the tubular vessel 150 can be cut along seal 152 to separate the tissue 150 and form a gap in the tissue 150 therebetween.

It is envisioned that by making the electrode assembly 21 disposable, the electrode assembly 21 is less likely to become damaged since it is only intended for a single operation and, therefore, does not require cleaning or sterilization. As a result, the functionality and consistency of the sealing components, e.g., the electrically conductive surface 312 (and 322) and electrically insulating layer 211 (and 221) and jaw overmolding 314 (and 324) will assure a uniform and quality seal and provide a tolerable and reliable reduction of thermal spread across tissue. Alternatively, the entire electrosurgical instrument may be disposable, which, again, will assure a uniform and quality seal with minimal thermal spread.

Figure 7:
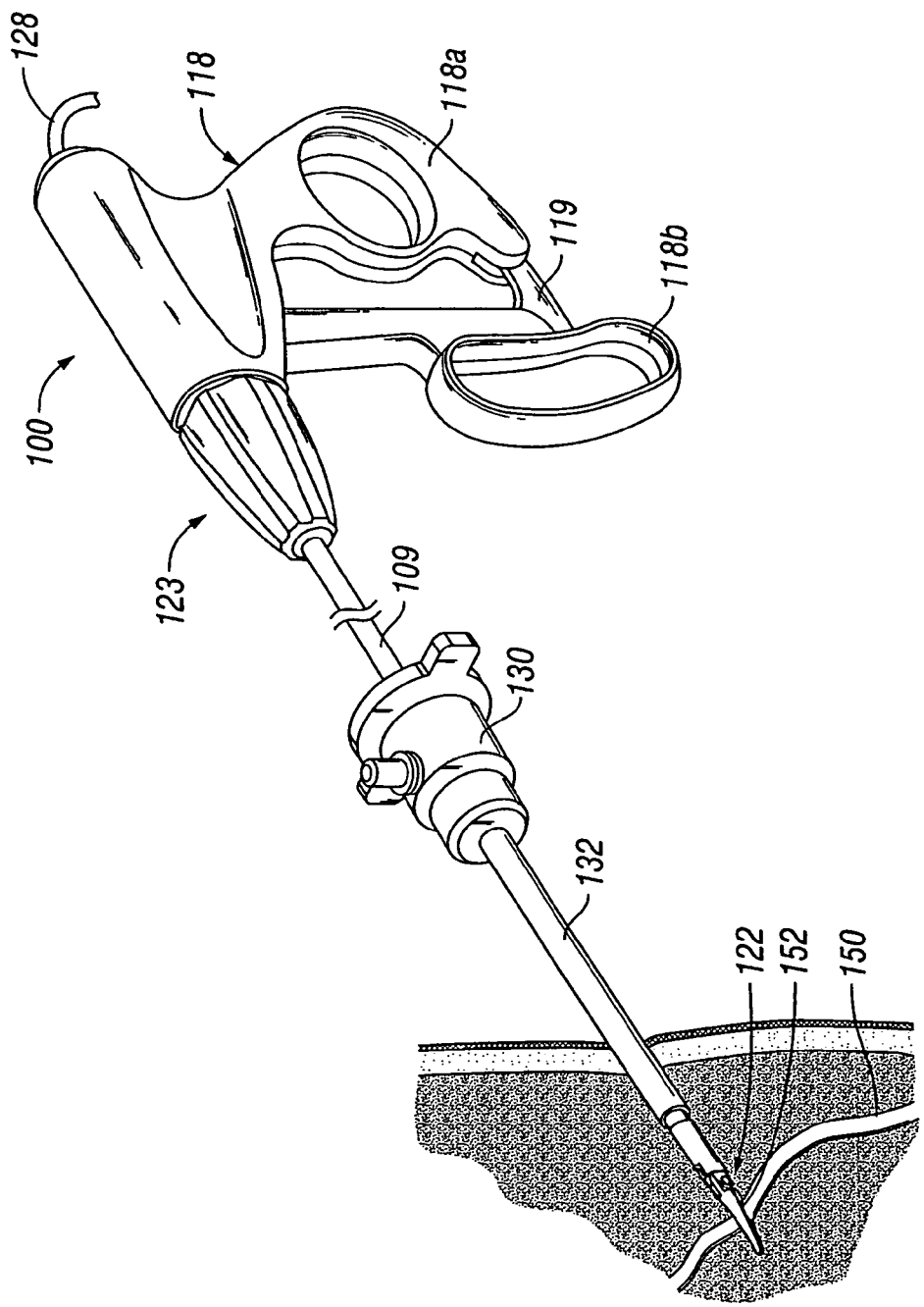
FIG. 7 is a perspective view of an endoscopic version of the present disclosure showing the operative motion of the instrument to effect sealing of a tubular vessel.

FIG. 7 shows an endoscopic bipolar instrument 100 during use wherein movement of a handle assembly 128 applies clamping force on the tubular tissue 150 to effect a seal 152. As shown, a shaft 109 and an end effector assembly or electrode assembly 122 are inserted through a trocar 130 and cannula 132 and a handle assembly 118 is actuated to cause opposing jaw members of the electrode assembly 122 to grasp tubular vessel 150 therebetween. More particularly, a movable handle 118b is moved progressively towards a fixed handle 118a, which, in turn, causes relative movement of the jaw members from an open, spaced-apart position to a closed, sealing position. A rotating member 123 allows the user to rotate the electrode assembly 122 into position about the tubular tissue 150 prior to activation. End effector assembly 122 may include first and second electrode jaw members 310 and 320, respectively, as described previously.

After the jaw members 310 and 320 are closed about the tissue 150, the user then applies electrosurgical energy via connection 128 to the tissue 150. By controlling the intensity, frequency and duration of the electrosurgical energy applied to the tissue 150, the user can either cauterize, coagulate/desiccate seal and/or simply reduce or slow bleeding with minimal collateral or thermal damage to surrounding tissue.

An electrosurgical forceps such as, for example but not limited to, open bipolar instrument 10 and end effector assembly 1000 (see FIG. 6) and endoscopic bipolar instrument 100 and electrode assembly 122 (see FIG. 7), may include a knife channel for passage of a knife for cutting tissue during surgical procedures.

From the foregoing and with reference to the various figure drawings, those skilled in the art will appreciate that certain modifications can also be made to the present disclosure without departing from the scope of the present disclosure. For example, although it is preferable that electrodes 310 and 320 meet in parallel opposition and, therefore, meet on the same plane, in some cases it may be preferable to slightly bias the electrodes 310 and 320 to meet each other at a distal end such that additional closure force on the handles 16 and 18 is required to deflect the electrodes in the same plane. It is envisioned that this could improve seal quality and/or consistency.

Although it is preferable that the electrode assembly 21 include housing 71 and cover plate 80 to engage mechanical forceps 20 therebetween, in some cases it may be preferable to manufacture the electrode assembly 21 such that only one piece, e.g., housing 71 is required to engage mechanical forceps 20.

The outer surface of the end effectors may include a nickel-based material, coating, stamping, metal injection molding that is designed to reduce adhesion between the end effectors (or components thereof) with the surrounding tissue during or after sealing.

One embodiment of the foregoing method for manufacturing the jaw member 310 or 320 of an end effector assembly 1000 or 122 for use with an electrosurgical instrument 10 or 100, respectively, includes the steps of providing an electrically conductive tissue engaging plate 312 or 322 and a jaw support 319 or 329 (See FIGS. 2A and 3A); covering one side 312' or 322' of the electrically conductive tissue engaging plate 312 or 322 with an electrically insulative, thermally non-degrading coating 211 or 221; placing and securing the electrically conductive tissue engaging plate 312 or 322 and the jaw support 319 or 329 into a jaw mold (not shown) and introducing a liquid substance (not shown) into the jaw mold and allowing the liquid substance (not shown) to cure around the electrically conductive tissue engaging plate 312 or 322 and the jaw support 319 or 329. The liquid substance may be selected from the group consisting of liquid crystal polymer, thermoplastic polymer, epoxy and silicone. The coating 211 or 221 of the covering step may be of uniform thickness across the electrically conductive tissue engaging plate 312 or 322. In addition, the coating 211 or 221 of the covering step may include a thickness that provides the gap-set "G" between the electrically conductive tissue engaging plate 312 or 322 and the jaw support 319 or 329 during the introducing step (see FIG. 6).

In another particularly useful embodiment, as best illustrated in FIGS. 2A and 3A, the insulating layer 211 and 221 of electrode 310 and 320 is attached to opposite side seal surface 312' and 322' via application of adhesive 251. As discussed previously, the adhesive 251 may include a material that includes polyurethane or other materials. Again, in this case, the application of the jaw overmolding 314 and 324 over the insulating layer 211 and 221, respectively, is optional. Those skilled in the art will recognize that adhesive 251 may be applied in a similar manner to the insulating layer 221 of electrode 320 and seal surface 322.

Again, by applying a coating of electrically insulating layer 211 and 221 onto one side 312' and 322' of electrically conductive seal plates 312 and 322, respectively, enhanced thermal and electrical properties are provided so as to increase electrical and thermal isolation during activation and may be dimensioned to regulate the gap distance "G" to within a preferred gap range as described in more detail previously with respect to FIG. 6.

More particularly, referring to FIG. 6, one embodiment relating to the foregoing method for manufacturing the jaw member 110 or 120 of the end effector assembly 1000 for use with the electrosurgical instrument 10 or 100. The method includes the steps of: providing the electrically conductive tissue engaging plate 312 or 322 and the jaw support 319 or 329; covering one side 312' or 322' of the electrically conductive tissue engaging plate 312 or 322 with the electrically insulative, thermally non-degrading coating 211 or 221; and securing the side 312' or 322' of the electrically conductive tissue engaging plate 312 or 322 onto the jaw support 319 or 329 with the adhesive 251. The coating 211 or 221 of the covering step may be of uniform thickness across the electrically conductive tissue engaging plate 312 or 322. The coating 211 or 221 of the covering step may include a thickness that provides the gap-set "G" between the electrically conductive tissue engaging plate 312 or 322 and the jaw support 319 or 329 during the introducing step (see FIG. 6).

While more than one embodiment of the disclosure has been described, it is not intended that the disclosure be limited thereto, as it is intended that the disclosure be as broad in scope as the art will allow and that the specification be read likewise. Therefore, the above description should not be construed as limiting, but merely as exemplifications of a preferred embodiment. Those skilled in the art will envision other modifications within the scope and spirit of the claims appended hereto.

What is claimed is:

1. A method for manufacturing a jaw member of an end effector assembly for use with an electrosurgical instrument, the method comprising the steps of:
   providing an electrically conductive tissue engaging plate, said electrically conductive tissue engaging plate having vertically-extending edges extending about a periphery and along a length thereof of said electrically conductive plate, and a jaw support;
   covering one side of the electrically conductive tissue engaging plate and said vertically-extending edges with an electrically insulative, thermally non-degrading coating;
   placing the electrically conductive tissue engaging plate, the electrically insulative, thermally non-degrading coating, and the jaw support into a jaw mold; and
   introducing a liquid substance into the jaw mold and allowing the liquid substance to cure around the electrically conductive tissue engaging plate, the electrically insulative, thermally non-degrading coating and the jaw support to form an overmolding around the electrically conductive tissue engaging plate, around the electrically insulative, thermally non-degrading coating, and around the jaw support.

2. A method according to claim 1 wherein the electrically insulative, thermally non-degrading coating of the covering step is selected from a group of materials consisting of flame sprayed ceramic, vapor deposition polymer, an oxide layer, and an anodized coating.

3. A method according to claim 1 wherein the electrically insulative, thermally non-degrading coating has a uniform thickness across the electrically conductive tissue engaging plate.

4. A method according to claim 1 wherein the electrically insulative, thermally non-degrading coating has a thickness that provides a gap-set between the electrically conductive tissue engaging plate and the jaw support during the introducing step.

* * * * *